(12) United States Patent
Leitner et al.

(10) Patent No.: US 7,318,827 B2
(45) Date of Patent: Jan. 15, 2008

(54) OSTEOTOMY PROCEDURE

(75) Inventors: Francois Leitner, Uriage (FR);
Jean-Baptiste Pinzuti, Grenoble (FR)

(73) Assignee: Aesculap AG & Co. KG, Tuttlingen (DE)

( * ) Notice: Subject to any disclaimer, the term of this patent is extended or adjusted under 35 U.S.C. 154(b) by 644 days.

(21) Appl. No.: 10/307,594

(22) Filed: Dec. 2, 2002

(65) Prior Publication Data
US 2004/0106926 A1    Jun. 3, 2004

(51) Int. Cl.
*A61F 5/00* (2006.01)
*A61B 5/05* (2006.01)

(52) U.S. Cl. .................................... 606/87; 600/427
(58) Field of Classification Search ............ 606/86, 606/87, 88, 89, 79, 96, 97, 102; 600/411, 600/416, 424, 425, 426, 427
See application file for complete search history.

(56) References Cited

U.S. PATENT DOCUMENTS

| | | | |
|---|---|---|---|
| 4,979,949 A * | 12/1990 | Matsen et al. ............... | 606/53 |
| 5,540,695 A | 7/1996 | Levy ........................... | 606/87 |
| 6,385,475 B1 | 5/2002 | Cinquin et al. | |
| 6,711,432 B1 * | 3/2004 | Weiss et al. ................ | 600/427 |
| 2002/0198451 A1 * | 12/2002 | Carson ........................ | 600/424 |

FOREIGN PATENT DOCUMENTS

| WO | WO 02/037935 | 10/2001 |
|---|---|---|
| WO | WO02/37935 | 5/2002 |

OTHER PUBLICATIONS

Clinical Paper entitled, "A Surgical Planning And Guidance System For High Tibial Osteotomy", authored by R.E. Ellis, Ph.D., C.Y. Tso, M.Sc., J.F.Rudan,M.D. and M.M. Harrison, M.D., published in Computer Aided Surgery, pp. 264-279 in 1999.
International Search Report generated by the European Patent Office—Authorized Officer: M. Angeli—and bearing mailing date of Apr. 6, 2004.
Tso et al., "A surgical planning and guidance system for high tibial osteotomies", MICCAI '98, LNCS, 1496:39-50 (1998).

* cited by examiner

*Primary Examiner*—Anuradha Ramana
(74) *Attorney, Agent, or Firm*—Synnestvedt & Lechner LLP

(57) ABSTRACT

An osteotomy resection procedure for removing a wedge from a bone utilizing a localization device. The localization device being used to track reference points associated with the bone, track surgical instruments, perform calculations to determine a resection angle for the wedge, and assist a surgeon in performing the procedure.

16 Claims, 5 Drawing Sheets

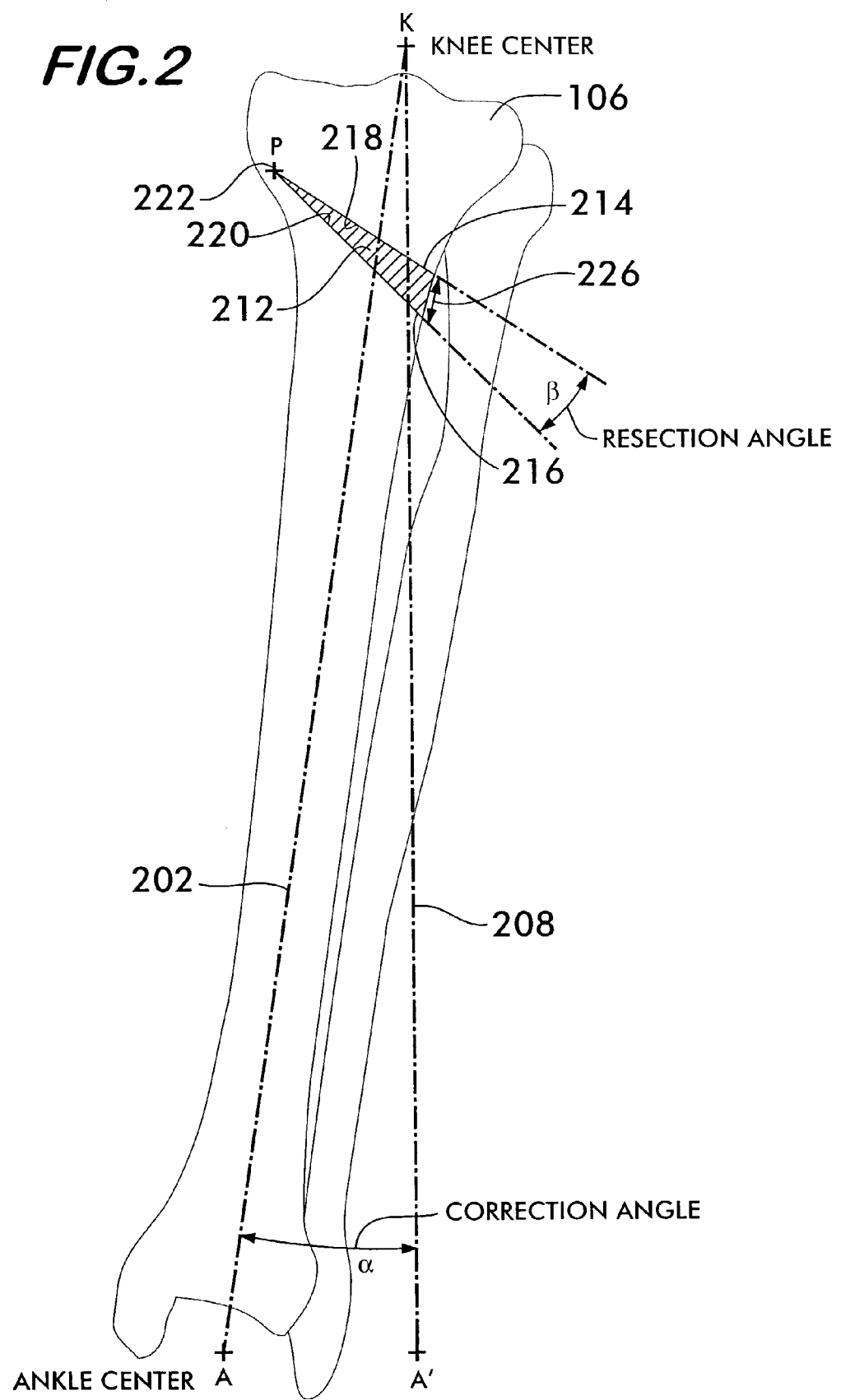

OSTEOTOMY PROCEDURE

FIELD OF THE INVENTION

The present invention relates to the field of medicine and, more particularly, to the field of osteotomy.

BACKGROUND OF THE INVENTION

An osteotomy is a surgical procedure in which a bone is divided or a piece of bone is excised. Typically, the procedure is performed to correct a deformity. For example, the procedure may be performed on a femur and/or tibia to correct deformities such as misalignments in the legs that lead to bow legs (outward bowing of the legs) and knock knees (inward bowing of the legs).

In a perfectly aligned leg, a line running through the center of the hip joint to the center of the ankle joint passes through the center of the knee joint. This is called the weight bearing axis of the knee. In people with improperly aligned legs, the weight bearing axis does not pass through the center of the knee, which may result in abnormal wear of the knee joint, thereby causing pain and leading to failure of the knee.

One of the solutions for this condition is to reshape the bones within the leg using an osteotomy procedure. The goal of the procedure is to realign the leg such that the weight bearing axis runs through the center of the knee. During the procedure, a wedge of bone is cut from a leg bone (e.g., the tibia and/or the femur). The wedge is formed by making a first cut into the bone at a first angle and a second cut into the bone at a second angle. After cutting, the wedge is removed and the remaining bone along the first and second cuts is brought together to reshape the bone, thereby realigning the leg. Finally, the bone is fixed with wires and/or screws and allowed to mend.

The determination of the location and angle of the first and second cuts is based largely on subjective analysis by the surgeon and, thus, is prone to error. Ideally, the first and second cuts will meet precisely at their maximum depth and the second cut will form an angle (i.e., a resection angle) with respect to the first cut that provides the proper amount of correction to the alignment of the leg when the wedge is removed and the cut surfaces are brought together. However, since there is a subjective component to the determination of the cuts, the cut surfaces may not meet precisely. If the cut surfaces do not meet precisely, gaps may be present when the bone is brought together at the cut surfaces, which can hinder mending. In addition, an incorrect resection angle will result in improper correction of the alignment of the leg.

Therefore, there is a need for methods of removing a wedge from a bone such that cut surfaces meet precisely and resection angles are accurately determined. The present invention fulfills this need among others.

SUMMARY OF THE INVENTION

The present invention provides an osteotomy resection procedure for removing a wedge from a bone. The present invention overcomes the aforementioned problem by utilizing a localization device during the procedure to precisely determine reference points associated with the bone (e.g., the center of joints on either side of the bone), track instruments, perform calculations (e.g., to determine the resection angle of the wedge), and provide a visual display for use in orienting instruments during the procedure. The localization device provides objective information for use during the procedure to minimize reliance on subjective analysis to determine the location and angle of cuts, thereby ensuring that cut surfaces meet precisely at a correct resection angle. The present invention is particularly useful, although not exclusively so, for removing wedges from bones within the leg to correct misalignment.

One aspect of the invention is a method for removing a wedge from a bone to reshape the bone, wherein, prior to removing the wedge, the bone extends between a first position corresponding to a first end of the bone and a second position corresponding to a second end of the bone and wherein, after removing the wedge, the second end of the bone is relocated to a third position such that a desired correction angle is produced between a first vector extending from the first position to the second position and a second vector extending from the first position to the third position. The method includes performing a first cut into the bone, the first cut having a depth; determining a pivot point within the bone, the pivot point located within the first cut; calculating a resection angle at the pivot point for the wedge with respect to the first cut to produce the desired correction angle; and performing a second cut into the bone, the second cut made with respect to the first cut at the resection angle and extending to at least about the pivot point, the first and second cuts defining the wedge.

Another aspect of the invention is method for removing a wedge from a bone extending between a first joint and a second joint to reshape the bone, the first joint coupling the bone on a first end to a first body and the second joint coupling the bone on a second end to a second body. The method includes determining the center of the first joint to obtain a first position; determining the center of the second joint to obtain a second position; performing a first cut into the bone, the first cut having a depth; determining a pivot point within the bone, the pivot point located at the depth of the first cut; calculating a resection angle for the wedge with respect to the first cut based on the pivot point, the first and second determined positions, and the desired correction angle, wherein, prior to removing the wedge, the bone extends between the first position and the second position and wherein, after removing the wedge, the second end of the bone is relocated to a third position such that a desired correction angle is produced between a first vector extending from the first position to the second position and a second vector extending from the first position to the third position; and performing a second cut into the bone at the resection angle, the second cut extending to at least about the pivot point, the first and second cuts defining the wedge.

In certain aspects of the invention, one or more steps are performed by a computer executing computer readable program code embodied in a computer readable medium.

BRIEF DESCRIPTION OF THE DRAWINGS

FIG. 2 is a diagram depicting the removal of a wedge from a tibia in accordance with the present invention;

DETAILED DESCRIPTION OF THE INVENTION

Figure 1:
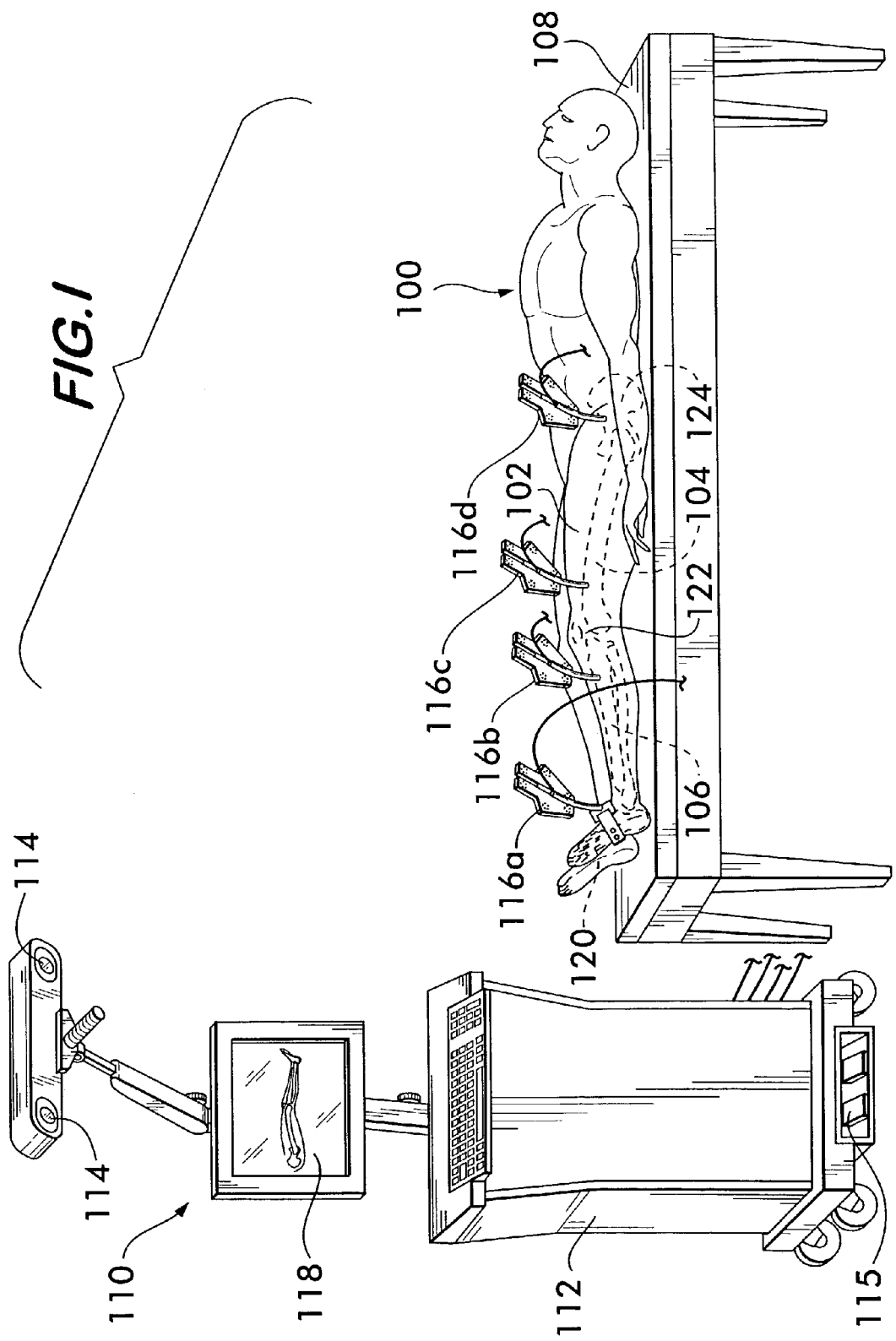
FIG. 1 is an illustration of a patient about to undergo an osteotomy procedure utilizing a localization device in accordance with the present invention.

In FIG. 1, a patient 100, who is to undergo an osteotomy procedure on a leg 102 to remove a wedge of bone from the femur 104 and/or the tibia 106 to realign the leg is illustrated schematically lying on an operating table 108. In addition, a localization device 110, which will be utilized during the procedure, is depicted. The localization device 110 is a surgical navigation system that includes a computer 112 loaded with software for surgical navigation, sensors 114 (e.g., cameras) coupled to the computer 112 and capable of detecting markers 116, a foot pedal for prompting the localization device 110 to store surgical navigation information, and a monitor 118 for displaying surgical navigation information to a surgeon to help the surgeon determine appropriate locations or alignments for cutting jigs and the like. The sensors 114 are positioned above and laterally from the patient 100 so that the patient's leg 102 is in the field of view of the sensors 114. In general, the markers 116 are fixedly mounted on bones and surgical instruments so that the localization device 110 can track the exact location and orientation of the bones and surgical instruments to which they are mounted. A description of a suitable localization device 110 is found in U.S. Pat. No. 6,385,475 to Cinquin et al., having a common inventor and commonly assigned to the same entity as the present application and incorporated herein by reference.

Prior to the procedure, the amount of correction needed to properly align the leg 102 is assessed using known techniques. In a preferred embodiment, first, the deformation of the leg 102 is measured using x-rays of the leg 102. Next, the amount of correction is determined based on the experience of the surgeon, the weight of the patient 100, and the laxity of the ligaments. Depending on the amount of correction needed, the surgeon may remove a wedge from the femur 104 and/or the tibia 106. For descriptive purposes, a procedure is described for removing a wedge from the tibia 106 to correct misalignment within the leg 102.

FIG. 2 depicts a detailed view of the tibia 106 within the leg 102 of FIG. 1 with like elements being identically numbered for use in describing the osteotomy procedure. In a general overview, first, the surgeon determines a correction angle, a, for the tibia 106 based on the amount of correction needed. The correction angle is an angle between an actual line 202 extending from the knee joint center K to the ankle joint center A before correction and a desired line 208 extending from the knee joint center K to a new ankle joint center A' after correction. It will be understood that the surgeon may select a correction angle, $\alpha$, that produces a small degree of over correction, e.g., typically less than about 2 degrees, to compensate for the weight of the patient 100 and the laxity of the ligaments. In a preferred embodiment, the desired line 208 for the tibia 106 corresponds to an ideal weight bearing axis, i.e., a straight line extending from the hip joint center (not shown) to the new ankle joint center A' and passing through the knee joint center K. To realign the leg 102 (FIG. 1), a wedge 212 having a resection angle, $\beta$, is cut from the tibia 106 by making a first cut 214 and a second cut 216 into the tibia 106 utilizing a localization device 110 (FIG. 1). The wedge 212 is then removed, thereby exposing a first cut surface 218 and a second cut surface 220. Finally, the first and second cut surfaces 218, 220 are brought together to reshape the tibia 106, thereby repositioning the actual line 202 of the tibia 106 such that it overlays the desired line 208. The procedure will next be described in detail with reference to FIGS. 1 and 2.

Initially, the knee joint center K and the ankle joint center A are determined. For this purpose, marking elements 116 are inserted into the femur 104 and the tibia 106 with bone screws, and attached to the foot 120, e.g., with a strap. To locate the ankle joint center A, the surgeon flexes the patient's ankle while the localization device 110 observes the foot marker 116a and the tibia marker 116b and collects points from these markers 116a, 116b during this motion. The computer 112 then calculates the ankle joint center A from the collected points. Next, the surgeon moves the patient's knee generally in a circle while the localization device 110 observes the femur marker 116c and the tibia marker 116b and the computer 112 calculates the knee joint center K from the collected points. Reference may be had to aforementioned U.S. Pat. No. 6,385,475 for a more detailed description of obtaining the joint centers using a surgical navigation system.

FIGS. 3A, 3B, 3C, and 3D depict a cutting jig 230, a saw 232, a check blade 234, and a pointer 248, respectively, which are surgical instruments that, with reference to FIGS. 1 and 2, will be referred to throughout the following discussion related to making the first and second cuts 214, 216 and determining the resection angle, $\beta$.

Figure 3A:
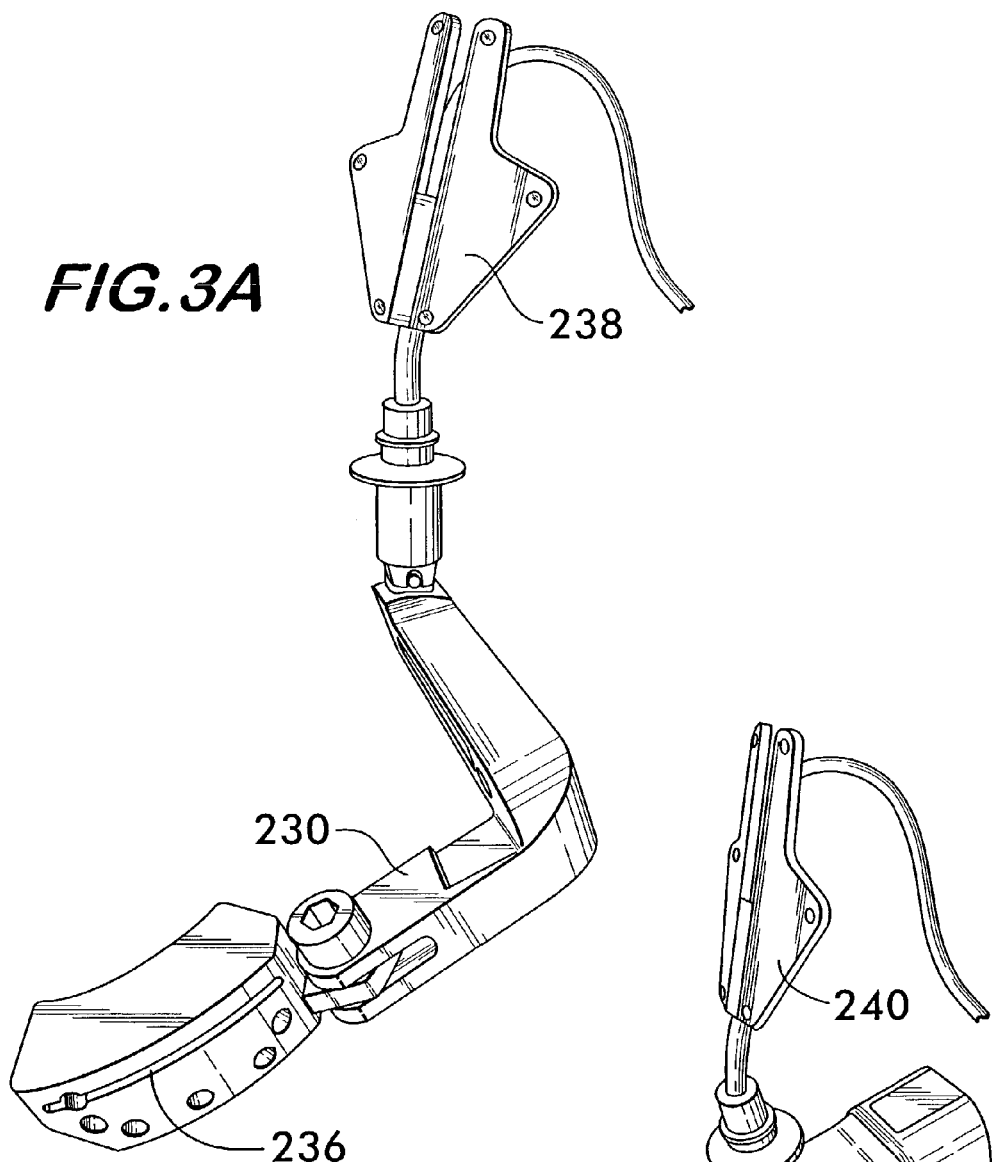
FIGS. 3A-3D depict surgical instruments for removing the wedge of FIG. 2.
Figure 3B:
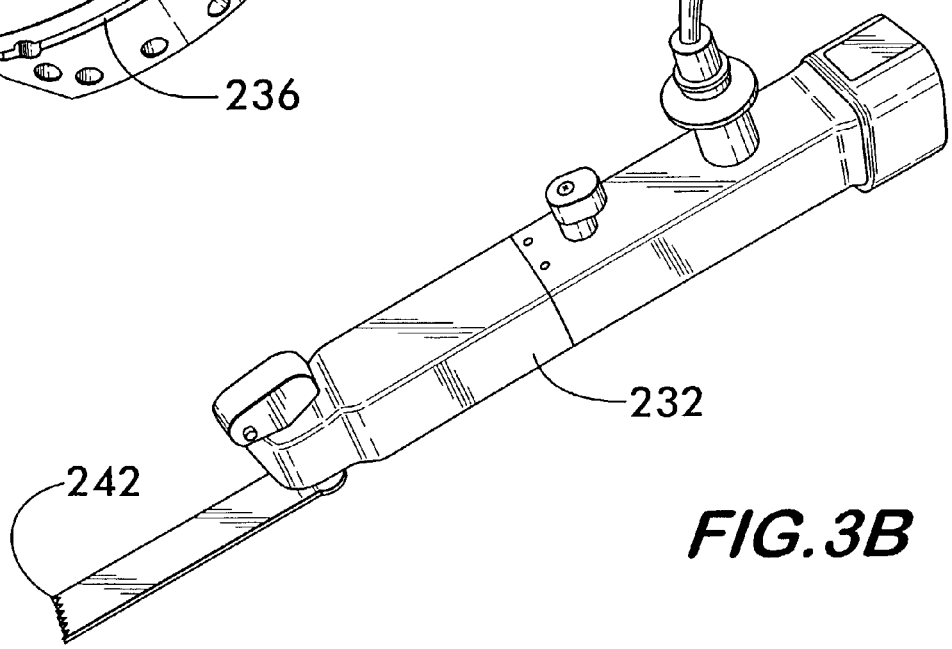
Figure 3C:
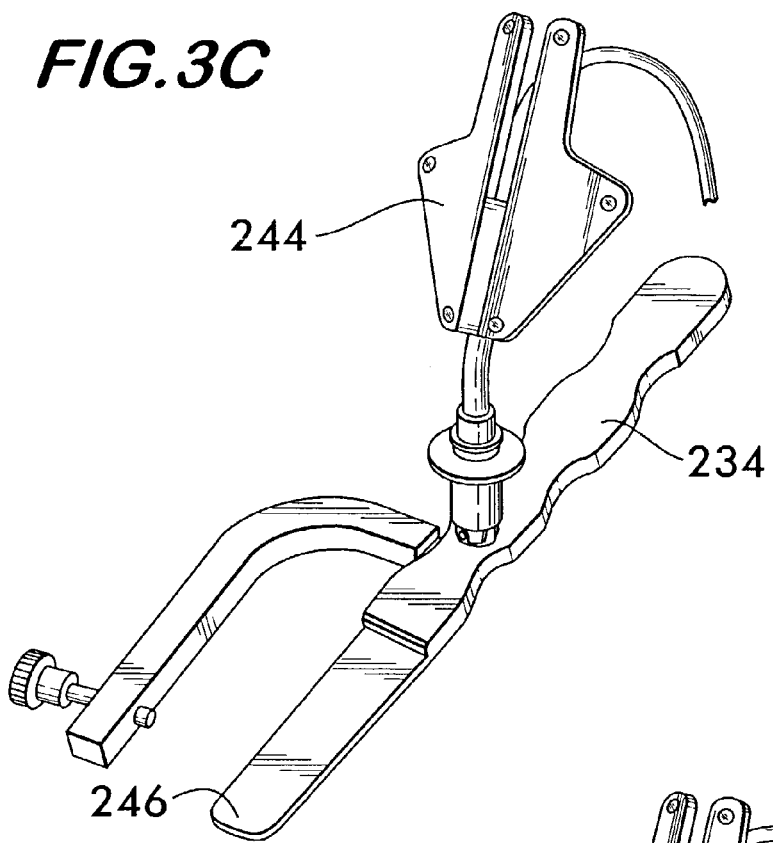
Figure 3D:
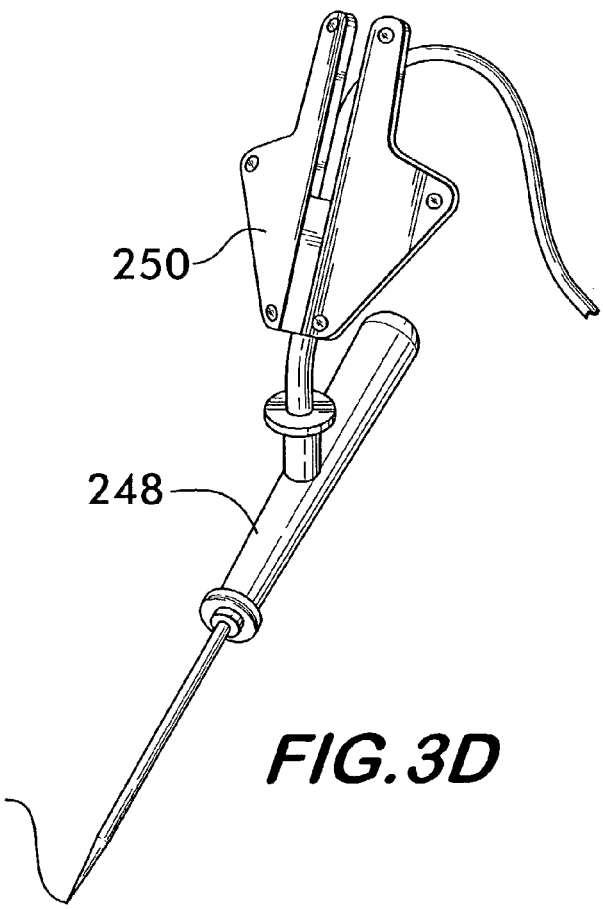

In preparation for making the first cut 214, a cutting jig 230 (FIG. 3A) will be positioned and attached to the tibia 106 by the surgeon. As depicted in FIG. 3A, the cutting jig 230 contains a guide 236 for guiding a saw 232 (FIG. 3B) and is capable of receiving a marker 238 so that it may be tracked by the localization device 110. The marker 238 is mounted on the cutting jig 230 in a predetermined way and the localization device 110 is preprogrammed with data that indicates the orientation and position of the cutting jig guide 236 relative to the marker 238 mounted on the cutting jig 230. The localization device 110 determines the orientation and position of the guide 236 relative to the tibia 106. The localization device 110 knows the position of the tibia 106 from the position of the marker 116b on the tibia. The cutting jig 230 is navigated using the localization device 110 and attached to the tibia 106 so that the guide 236 is positioned to guide the saw 232 (FIG. 3B) at a predefined angle. In certain embodiments, the predefined angle is approximately 90 degrees to the actual line 202 of the tibia 106 (i.e., parallel to the tibia plateau) and is made within an area extending between the knee center K and the lateral-medial ligament attachment on the tibia 106. This is referred to as an intra joint correction. In certain other embodiment, the predefined angle is approximately 45 degrees to the actual line 202 of the tibia 106 and is made outside of the area extending between the knee center K and the lateral-medial ligament attachment on the tibia 106. This is referred to as an extra joint correction. In a preferred embodiment, the guide 236 is further navigated such that it is located near the knee and a saw cutting tip 242 inserted through the guide 236 is capable of extending almost to the opposite side of the tibia 106.

The saw 232 (FIG. 3B) is a calibrated saw capable of accepting a marker 240 in a predetermined way so that the saw 232 may be tracked by the localization device 110 and is of a type conventionally used for cutting bones, e.g., a oscillating saw having an oscillating cutting tip. The localization device 110 is preprogrammed with data that indicates the orientation and position of the cutting tip 242 relative to the marker 240 mounted on the saw 232. The localization device 110 can then observe the marker 240 and determine the orientation and position of the cutting tip 242 relative to the tibia 106 during the procedure. In a preferred embodiment, prior to making the first cut 214, the saw 232 is inserted into the cutting jig 230 until the cutting tip 242 is in contact with the tibia 106. This position is then recorded by the localization device 110 to capture the entry point of the first cut 214 on the tibia 106 (for use in making the second cut 216, described in detail below). The recording of the position may be prompted by the surgeon through the depression of the foot pedal 115 associated with the localization device 110 when he/she has the saw 232 properly positioned.

To make the first cut 214, the saw cutting tip 242 (FIG. 3B) is inserted into the the cutting jig guide 236 (FIG. 3A) and moved (e.g., by a surgeon) along a path defined by the cutting jig guide 236. Preferably, as the saw 232 makes the first cut 214, the orientation of the saw 232 relative to the tibia 106 (e.g., in axial, frontal, and sagittal views) and the distance between the cutting tip 242 and the opposite edge of the tibia 106 are displayed on the monitor 118 of the localization device 110 to assist the surgeon in making the first cut 214.

After the first cut 214 is completed, the check blade 234 (FIG. 3C) is inserted into the first cut 214 to check the orientation and depth of the first cut 214. The check blade 234 is a calibrated tool capable of receiving a marker 244 so that it may be tracked by the localization device 110. The marker 244 is mounted on the check blade 234 in a predetermined way and the localization device 110 is preprogrammed with data that indicates the orientation and position of a check blade tip 246 relative to the marker 244 mounted on the check blade 234. The localization device 110 observes the marker 244 to determine the orientation and position of the check blade tip 246 relative to the tibia 106. Preferably, the check blade tip 246 is inserted fully into the first cut 214 and the localization device 110 is made to record the angle and depth of the first cut 214, e.g., by depressing a foot pedal 115. In a preferred embodiment, the osteotomy pivot point P for the osteotomy procedure is located at the recorded depth of the first cut 214.

Once the osteotomy pivot point P and the angle of the first cut 214 are recorded, the resection angle, $\beta$, for the wedge 212 is calculated by the localization device 110 based on the correction angle, $\alpha$, for the tibia 106 and the location of the osteotomy pivot point P. The calculated resection angle, $\beta$, is then used to guide the surgeon for making the second cut 216. It will be recognized by those skilled in the art that the correction angle, $\alpha$, is not the same as the resection angle, $\beta$, because the knee center K and the osteotomy pivot point P are not co-located. In addition, it will be recognized that the wedge thickness 226 at the surface of the tibia 106 will be different for different osteotomy pivot points P.

Figure 4:
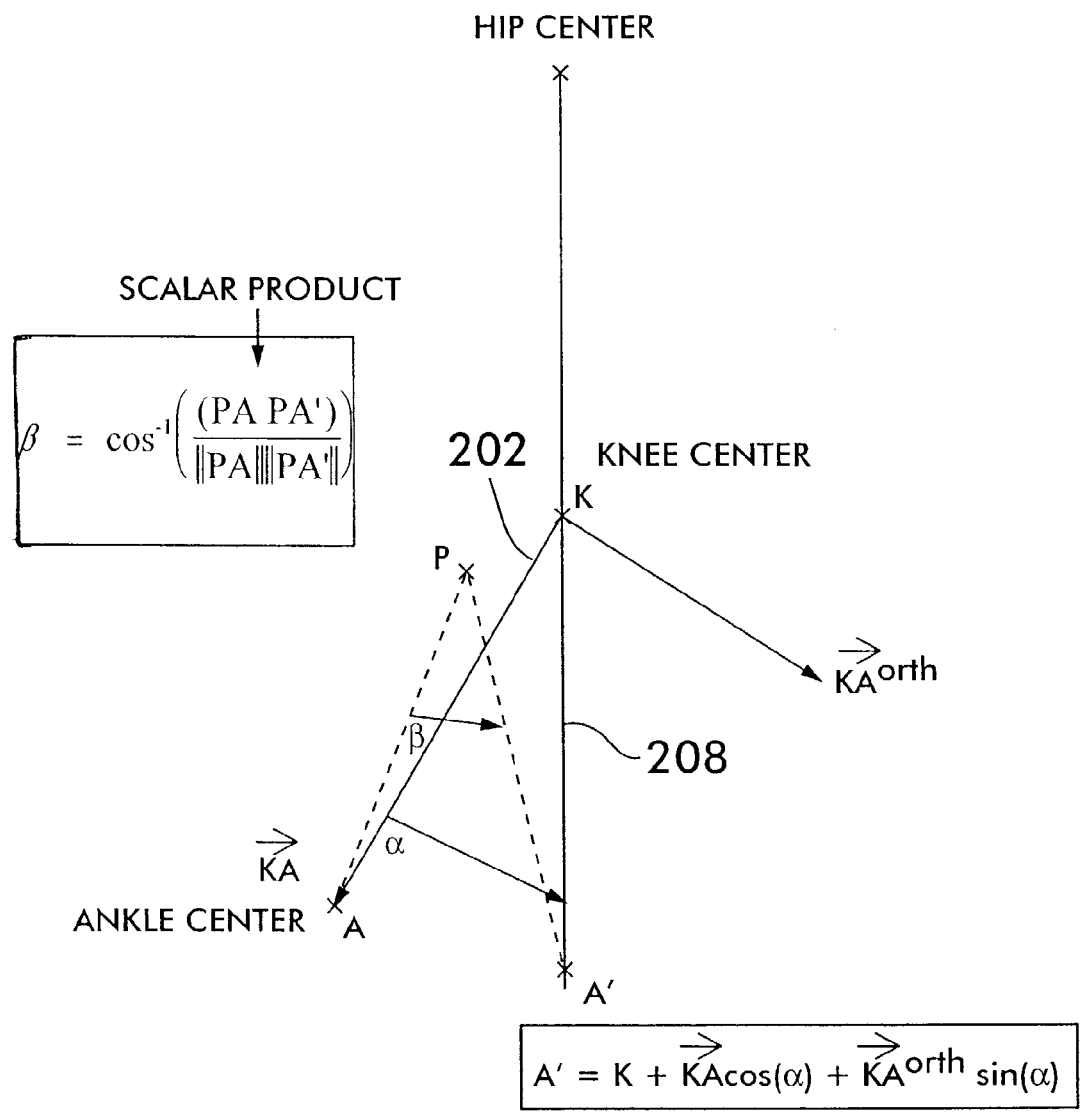
FIG. 4 is line diagram representing the calculations for determining the resection angle for the wedge of FIG. 2.

A preferred method for determining the resection angle, $\beta$, for use in making the second cut in the tibia 106 of FIG. 2 is illustrated in FIG. 4 with like elements being identically labeled. The correction angle, $\alpha$, is the angle formed between a vector extending from the knee joint center K to the ankle joint center A (i.e., KA) and a vector extending from the knee joint center K to the corrected ankle joint center A' (i.e., KA'), which is the angle required to reposition the actual line 202 of the tibia 106 (FIG. 2) onto the desired line 208 of the tibia 106. In order to determine the resection angle, $\beta$, (i.e., the angle about the osteotomy pivot point P required to reposition the ankle joint center from A to A') the position of the new ankle joint center A' must first be determined. It will be recognized by those skilled in the art that the resection angle, $\beta$, as depicted in FIG. 4 is equivalent to the resection angle depicted in FIG. 2. The position of the new ankle joint center A' with reference to the knee joint center K is given by the following equation:

$$A' = K + KA \cos(\alpha) + KA^{ortho} \sin(\alpha), \quad (1)$$

where $KA^{ortho}$ is of the same magnitude and orthogonal to KA. Once the position of the new ankle joint center A' is determined, the resection angle, $\beta$, can be determined using the following equation:

$$\beta = \cos^{-1}\left(\frac{(PA \; PA')}{\|PA\|\|PA'\|}\right); \quad (2)$$

where PA is a vector extending from the osteotomy pivot point P to the ankle joint center A prior to the osteotomy procedure and PA' is a vector extending from the osteotomy pivot point P to the new ankle joint center A' after the osteotomy procedure.

Referring back to FIGS. 1 and 2, before the second cut 216 is made, an entry point for the second cut 216 into the tibia 106 is selected by the surgeon. In a preferred embodiment, the surgeon uses a calibrated pointer 248 (FIG. 3D) capable of receiving a marker 250 for tracking by the localization device 110 to palpate various positions on the surface of the tibia 106 in order to identify an entry point for the second cut 216 that will produce the calculated resection angle, $\beta$. The localization device 110 is preprogrammed with data that indicates the orientation and position of the pointer tip (FIG. 3D) relative to the marker 250. The localization device 110 can then observe the marker 250 and determine the position and orientation of the pointer tip 252 relative to the tibia 106.

During the palpation of the tibia 106, the localization device 110 displays on the monitor 118 the resulting wedge angle and wedge thickness, i.e., the distance from the first cut 214 entry point (described above), that would result if the second cut 216 were commenced at the location of the pointer tip 252 and ended at the point P defined by the first cut 214. The surgeon moves the pointer tip 252 along the surface of the tibia 106 until the location of the pointer tip 252 results in the display of the calculated resection angle, $\beta$, by the localization device 110. The location that produces the calculated resection angle, $\beta$, is then selected by the surgeon and stored by the localization device 110, e.g., by depressing a foot pedal 115 coupled to the localization device 110.

In preparation for making the second cut 216, the cutting jig 230 (FIG. 3A) is positioned and attached to the tibia 106. In a preferred embodiment, the cutting jig 230 is initially attached to the check blade 234 inserted into the first cut 214. As described above, the cutting jig 230 (FIG. 3A) contains a guide 236 for guiding the saw 232 (FIG. 3B) and is capable of accepting a marker 238 so that the orientation and position of the cutting jig guide 236 may be tracked relative to the marker 238 mounted on the jig 230 and relative to the tibia 106. The cutting jig 230 is navigated using the localization device 110 so that the guide 236 is positioned to guide the saw cutting tip 242 (FIG. 3B) such that it enters the tibia 106 at the location selected by the surgeon through palpation, intersects the first cut 214 at the osteotomy pivot point P, and has an angle with reference to the first cut 214 equal to that of the calculated desired resection angle, $\beta$. After navigation, the cutting jig 230 is attached to the tibia 106 and its position is recorded by the localization device 110, e.g., by depressing a foot pedal 115 coupled to the localization device 110. In the preferred embodiment, the check blade 234 remains in the first cut and the cutting jig 230 remains attached to the check blade 234 to provide stability during the second cut.

To make the second cut 216, the saw cutting tip 242 (FIG. 3B) is inserted into the cutting jig guide 236 (FIG. 3A), activated, and moved (e.g., by a surgeon) along a path defined by the cutting jig guide 236. As described above, the saw 232 is a calibrated saw capable of receiving a marker 240 for tracking the orientation and position of the cutting tip 242 relative to the marker 240 mounted on the saw and relative to the tibia 106. Preferably, as the saw 232 makes the second cut 216, the orientation of the saw relative to the tibia 106 (e.g., in the frontal view) and the distance between the cutting tip 242 and the osteotomy pivot point P are displayed on the monitor 118 of the localization device 110 of FIG. 1 to assist the surgeon in making the second cut 216.

After the second cut 216 is completed, the check blade 234 is inserted into the second cut 216 to check the orientation and depth of the second cut 216 for use in clinical studies, e.g., for comparison to post operative X-rays. As described above, the check blade 234 is a calibrated tool capable of receiving a marker 244 for tracking by the localization device 110 to indicate the orientation and position of the check blade tip 246 relative to the marker 244 mounted on the check blade 234 and relative to the tibia 106. Preferably, the check blade tip 246 is inserted fully into the second cut 216 and the localization device 110 records the angle and depth of the second cut 216, e.g., upon depression of the foot pedal 115.

After the second cut 216 is made and checked, the resulting wedge 212, the cutting jig 230, and the tibia and femur markers 116b, c are removed. The procedure is then completed in a known manner by drawing together and securing the first and second cut surfaces 218, 220 along the first and second cuts 214, 216, thereby repositioning the ankle joint center from A to A' such that the actual line 202 overlays the desired line 208.

Referring back to FIG. 1, an essentially identical procedure can be performed on the femur 104. The femur 104 is reshaped by cutting a wedge from the femur 104 to reposition an actual line of the femur 104 extending between the center of the knee 122 and a center of the hip 124 to overlay a desired line extending between the center of the knee 122 and the center of the hip 124 after the wedge is removed and the cut surfaces are brought together.

For an osteotomy procedure performed on the femur 104, initially, the center of the joints on either side of the femur 104 are determined, i.e., the center of the knee 122 and the center of the hip 124. For this purpose, marking elements 116 are inserted into the femur 104, the tibia 106, and, optionally, the hip 124. The center of the knee 122 is located as described above in reference to the tibia 106. The center of the hip 124 is determined by either inserting a marker 116d into the hip 124 of the patient 100 and observing the femur marker 116c and the hip marker 116d or by limiting the movement of the hip 124 and observing the femur marker 116c only.

The remainder of the procedure for removing a wedge from the femur 104 is similar to the procedure described above for removing a wedge of bone from the tibia 106 and will be readily apparent to those skilled in the art

Having thus described a few particular embodiments of the invention, various alterations, modifications, and improvements will readily occur to those skilled in the art. For example, the markers used on the cutting jig, saw, check blade, and pointer may be one marker that is alternately attached to these devices as needed or may be a plurality of markers. In addition, although the procedure has been described with reference to correcting the alignment of a human leg, it is contemplated that the procedure can be applied to essentially any bone such as bones within an arm and may be used to correct deformities in animals as well as humans. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A localization device for use in an osteotomy procedure to remove a wedge from a bone by making first and second cuts in the bone to reshape said bone, wherein, prior to removing said wedge, said bone extends between a first position corresponding to a first end of said bone and a second position corresponding to a second end of said bone and wherein, after removing said wedge, said second end of said bone is relocated to a third position such that a desired correction angle is produced between a first vector extending from the first position to the second position and a second vector extending from the first position to the third position, said device comprising:

sensors for sensing information corresponding to the locations of markers associated with one or more of the bones and one or more surgical instruments;

a computer coupled to said sensors for tracking the markers;

means for recording an angle and depth of the first cut;

means for determining a pivot point within the recorded first cut in the bone; and means for calculating a resection angle for making the second cut relative to the recorded first cut that will produce the desired correction angle when the wedge is removed from the bone.

2. The localization device of claim 1, further comprising: means for guiding the second cut relative to the first cut so as to produce the calculated resection angle.

3. The localization device of claim 2 wherein said means for recording an angle and depth of the first cut comprises:

markers trackable by said localization device for mounting to said bone in order to permit tracking of said reference points associated with said bone;

a first cut cutting jig having a guide, said cutting jig capable of receiving a marker for use by said localization device in orienting said guide with respect to said bone;

a saw having a cutting tip insertable into said guide for making said first cut, said saw capable of receiving a marker for use by the localization device in tracking said cutting tip with respect to the bone; and a display device adapted to generate a display indicating the position of said cutting tip with respect to the bone during the cutting of the bone to provide visual assistance for performing said first cut.

4. The localization device of claim 3 wherein said means for guiding the second cut relative to the first cut comprises:

a second cut cutting jig having a guide, said second cut cutting jig capable of receiving a marker for use by the localization device in orienting said second cut cutting jig guide with respect to said bone;

a second saw having a cutting tip insertable into said second cut cutting jig guide for making said second cut, said second saw capable of receiving a marker for use by the localization device in orienting said cutting tip with respect to said bone; and wherein said display is further adapted to generate a display indicating the position of the cutting tip of said second saw during said second cut with respect to the bone to provide visual assistance for performing said second cut.

5. The localization device of claim 2 wherein said means for recording an angle and depth of the first cut comprises:

means for obtaining reference points associated with the bone using said localization device;

means for tracking a first cut cutting jig having a guide relative to said bone, said cutting jig capable of receiving a marker for use by the localization device in orienting said guide with respect to the bone; and means for tracking a saw having a cutting tip, said saw capable of receiving a marker for use by the localization device in tracking said cutting tip with respect to the bone; and means for generating a display indicating the position of said cutting tip with respect to the bone during the cutting of the bone to provide visual assistance for performing said first cut.

6. The localization device of claim 5 wherein said means for guiding the second cut comprises:

means for tracking a second cut cutting jig having a guide, said second cut cutting jig capable of receiving a marker for use by the localization device in orienting said second cut cutting jig guide with respect to the bone, so that said second cut may be performed such that said second cut will intersect said first cut at said pivot point at the resection angle with respect to said first cut; and means for tracking a second saw having a cutting tip insertable into said second cut cutting jig guide for making said second cut, said saw capable of receiving a marker for use by said localization device in orienting said cutting tip of said second saw with respect to the bone; and means for displaying a representation indicating the position of the cutting tip of said second so with respect to the bone during the cutting of the bone to provide visual assistance for performing said second cut.

7. The localization device of claim 2, wherein said guiding means comprises at least:

a visual display coupled to said computer for guiding a surgeon during the osteotomy procedure.

8. The localization device of claim 1, wherein said means for calculating said resection angle comprises at least means for solving the equation:

$$\beta = \cos^{-1}\left(\frac{(PA\ PA')}{\|PA\|\|PA'\|}\right);$$

where β is said resection angle, PA is a vector extending from said pivot point to the second position, and PA' is a vector extending from said pivot point to the third position, wherein said pivot point is supplied by the localization device.

9. The localization device of claim 1, wherein said means for calculating said resection angle comprises at least means for determining $$A'=K+KA\cos(\alpha)+KA^{ortho}\sin(\alpha)$$

where A' is the third position, K is the first position, KA is a vector extending from the first position to the second position, $KA^{ortho}$ is a vector of equal magnitude and orthogonal to KA, and α is the desired correction angle.

10. The localization device of claim 9, wherein said means for calculating said resection angle further comprises at least means for solving the equation:

$$\beta = \cos^{-1}\left(\frac{(PA\ PA')}{\|PA\|\|PA'\|}\right);$$

where β is said resection angle, PA is a vector extending from said pivot point to the second position, and PA' is a vector extending from said pivot point to the third position, wherein said pivot point is supplied by said localization device.

11. The localization device of claim 1 wherein the means for recording an angle and depth of the first cut comprises:

means for determining an axis of said bone using the localization device and the markers mounted to the bone; and means for guiding a cutting jig for making the first cut having a marker mounted thereon relative to the bone using the localization device.

12. The localization device of claim 11 wherein the means for recording an angle and depth of the first cut further comprises:

means for generating a display showing the axis and the position of the cutting jig relative to the axis.

13. The localization device of claim 12 further comprising:

means for generating a display showing the wedge angle that would result if the second resection cut were commenced at the location pointed to by a tracked pointer and ended at the pivot point.

14. The localization device of claim 1 wherein said means for calculating a resection angle comprises:

means for determining the location of the third position with reference to the first position; and means for calculating said resection angle based on said pivot point, said second point, said second position, and said third position.

15. The localization device of claim 1 wherein said means for determining a pivot point comprises:

a check blade insertable into said first cut, said check blade having a marker so that it may be tracked by said localization device;

means for observing said marker on said check blade via said localization device to determine the depth of said first cut;

means for recording said location corresponding to said depth of said first cut as said pivot point.

16. The localization device of claim 1 wherein said means for determining said pivot point comprises:

means for tracking a check blade that can be fully inserted into said first cut, said check blade having a marker so that it may be tracked by localization device;

means for observing said marker.

* * * * *